(12) United States Patent
Meier

(10) Patent No.: US 7,875,648 B2
(45) Date of Patent: Jan. 25, 2011

(54) N-(DIBENZ(B,F)OXEPIN-10-YLMETHYL)-N-METHYL-N-PROP-2-YNYLAMINE (OMIGAPIL) FOR THE TREATMENT OF CONGENITAL MUSCULAR DYSTROPHY OR MYOPATHY RESULTING FROM COLLAGEN VI DEFICIENCY

(75) Inventor: Thomas Meier, Basel (CH)

(73) Assignee: Santhera Pharmaceuticals (Schweiz) AG, Liestal (CH)

( * ) Notice: Subject to any disclaimer, the term of this patent is extended or adjusted under 35 U.S.C. 154(b) by 41 days.

(21) Appl. No.: 12/295,801

(22) PCT Filed: Apr. 4, 2007

(86) PCT No.: PCT/EP2007/003067

§ 371 (c)(1),
(2), (4) Date: Dec. 4, 2008

(87) PCT Pub. No.: WO2007/115776

PCT Pub. Date: Oct. 18, 2007

(65) Prior Publication Data

US 2009/0176867 A1 Jul. 9, 2009

(30) Foreign Application Priority Data

Apr. 5, 2006 (EP) .................. 06007217

(51) Int. Cl.
*A61K 31/335* (2006.01)
(52) U.S. Cl. .................................... 514/450
(58) Field of Classification Search ........ None
See application file for complete search history.

(56) References Cited

U.S. PATENT DOCUMENTS

| | | | |
|---|---|---|---|
| 5,780,244 A | 7/1998 | Engvall et al. | |
| 5,780,500 A | 7/1998 | Betschart et al. | |
| 5,780,501 A | 7/1998 | Betschart et al. | |
| 5,863,743 A | 1/1999 | Campbell et al. | |
| 7,078,379 B2 | 7/2006 | Rüegg | |

FOREIGN PATENT DOCUMENTS

| WO | WO 2007/022951 A1 | 3/2007 |
|---|---|---|
| WO | WO 97/45422 A1 | 12/2007 |

OTHER PUBLICATIONS

Andringa et al., *Neurobiology of Disease*, 14: 205-217 (2003).
Muck-Seler et al., *Current Drugs*, 3(5): 530-535 (2000).
McGowan et al., *Microscopy Research and Technique*, 51: 262-279 (2000).
Urtizberea, *European Neurology*, 43: 127-132 (2000).
Waldmeier et al., *Naunyn-Schmiedeberg's Arch Pharmacol*, 362: 526-537 (2000).

*Primary Examiner*—Phyllis G. Spivack
(74) *Attorney, Agent, or Firm*—Leydig, Voit & Mayer, Ltd.

(57) ABSTRACT

The invention relates to a method of treating muscular dystrophy, such as a muscular dystrophy or myopathy resulting from mutations in genes encoding collagen VI, in a mammal. The method involves administering of a compound of the formula (I)

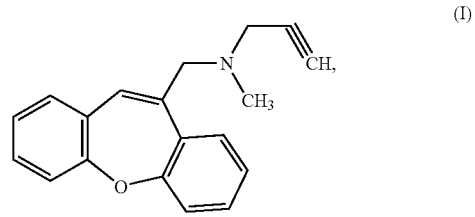

or a pharmaceutically acceptable addition salt thereof to the mammal.

11 Claims, 2 Drawing Sheets

N-(DIBENZ(B,F)OXEPIN-10-YLMETHYL)-N-METHYL-N-PROP-2-YNYLAMINE (OMIGAPIL) FOR THE TREATMENT OF CONGENITAL MUSCULAR DYSTROPHY OR MYOPATHY RESULTING FROM COLLAGEN VI DEFICIENCY

The present invention relates to the use of N-(dibenz(b,f) oxepin-10-ylmethyl)-N-methyl-N-prop-2-ynylamine or a pharmaceutically acceptable addition salt thereof for the prophylaxis and/or treatment of muscular dystrophy, preferably congenital muscular dystrophies, in particular congenital muscular dystrophy resulting from collagen VI deficiency such as Bethlem myopathy (BM) and Ullrich congenital muscular dystrophy (UCMD).

Congenital muscular dystrophy (CMD) is a heterogeneous group of muscle disorders characterized by muscle wasting, muscle fiber necrosis and fibrosis. The feature that makes it distinct from other muscular dystrophies, in particular to limb-girdle muscular dystrophies, is the early onset of symptoms at birth or within the first 6 months of life. CMDs are predominantly autosomally inherited diseases. Today, CMD is subgrouped into several distinct diseases based on their genetic origin (Kaplan J C (2006) Neuromuscular disorders: gene location; Neuromuscul. Disord. 16: 65). Generally, the prevalence of CMD is low (approx. 1–2.5×10−5).

CMD resulting from collagen VI deficiency clinically falls into two different syndromes, Ullrich congenital muscular dystrophy (Ullrich CMD, UCMD) which is clinically more severe and Bethlem myopathy (BM) which represents generally the milder form. Both clinical syndromes are termed CMD with Collagen VI deficiency. The estimated prevalence is below 1 in 100,000.

Bethlem myopathy (OMIM 158810) is an autosomal inherited myopathy with contractures caused by mutations in the gene encoding for collagen VI-A1 (Col6A1; OMIM 120220), collagen VI-A2 (Col6A2; OMIM 120240) or collagen VI-A3 (Col6A3; OMIM 120250). Several mutations in Col6A1-6A3 genes leading to Bethlem myopathy have been mapped and characterized (Lampe A K & Bushby K M D (2005); Collagen VI related disorders. J Med Genet. 42: 673-685). The classical phenotype is characterized by a variable clinical onset, and interfamilial variability being almost the rule (Bertini E, Pepe G., (2002) Collagen type VI and related disorders: Bethlem myopathy and Ullrich scleroatonic muscular dystrophy. Europ. J. Paediatric Neurol. 6:193-198). The clinical presentation in some adult patients can be simply with contractures and without weakness. The course of the disease is slowly progressing, and after the 5$^{th}$ decade about half of the patients need supportive means. Weakness involves proximal muscles more than distal muscles and extensors more than flexors. The most typical and frequent clinical sign of the disease is the presence of contractures (e.g. in interphalangeal joints, flexion contractures of the elbow and the ankles). Sometimes joint contractures can dominate the clinical picture.

Ullrich scleroatonic/congenital muscular dystrophy (UCMD; OMIM 254090) generally is characterized by mutations in the Col6A1, Col6A2 and Col6A3 genes (Lampe A K & Bushby K M D (2005); Collagen VI related disorders. J Med Genet. 42: 673-685). The disease presents as muscle weakness of early onset with proximal joint contractures and striking hyper-elasticity of the distal joints as well as protruding calcanei. Weakness is profound and children typically either never achieve the ability to walk independently, or walk independently for short periods only. Intelligence is normal. With progression of the disease, there is typically development of spinal rigidity and scoliosis and variable proximal contractures, while with time the distal hyperlaxity can give way to marked long finger flexion contractures and tight Achilles tendons. Respiratory failure in the first or second decade is a common cause of death unless treated with nocturnal respiratory support, but cardiac involvement is not documented to date. Other distinctive features observed in UCMD patients are congenital hip dislocations and a transient kyphotic deformity at birth as well as follicular hyperkeratosis and the tendency to keloid or "cigarette paper" scar formation (Lampe A K & Bushby K M D (2005); Collagen VI related disorders. J Med Genet. 42: 673-685).

Treatment for patients with BM and UCMD is supportive and follows identical principles, but depends in its intensity on the severity of symptoms and the age of onset. Children with a severe UCMD phenotype require active management as soon as the diagnosis is established, to promote mobility and independence. Early mobilization in a standing frame is important to achieve upright posture and protect against the development of scoliosis and other contractures. The contractures of UCMD patients in particular tend to be aggressive and may require surgical release. Scoliosis often develops in UCMD patients in the first or second decade of life and may require active management including spinal surgery to prevent progression. Regular assessments of respiratory function, including spirometry and overnight pulse oximetry studies, is important for all patients with collagen VI related disorders (Wallgren-Pettersson C., et al. (2004); 117$^{th}$ ENMC workshop: ventilatory support in congenital muscular disorders—congenital myopathies, congenital muscular dystrophies, congenital myotonic dystrophy and SMA. Neuromuscul. Disord 14:56-69). Respiratory support with nocturnal ventilation usually becomes necessary in the first or second decade for UCMD patients and can be effective in reducing symptoms, promoting quality of life, and allowing normal schooling (Mellies U et al. (2003) Long-term noninvasive ventilation in children and adolescents with neuromuscular disorders. Europ. Respir. J 22:631-636). In BM, respiratory failure with diaphragmatic involvement may supervene even before loss of ambulation, and symptoms of nocturnal hypoventilation. Prophylaxis of chest infections with influenza and pneumococcal vaccination and physiotherapy, as well as early and aggressive use of antibiotics, may prevent further respiratory problems in both BM and UCMD. In addition feeding difficulties in UCMD patients can manifest as failure to thrive or excessive time taken to finish eating a meal. Consultation with a nutrition specialist may be needed to boost energy intake; for serious problems, feeding by gastrostomy may be the best solution to promote a normal weight gain.

The problem underlying the present invention is to provide a compound which is suitable for the prophylaxis and/or treatment of muscular dystrophy resulting from mutations in the collagen VI gene resulting in a continuum of clinical manifestations with Bethlem myopathy (BM) at the mild end of the spectrum of clinical symptoms and Ullrich congenital muscular dystrophy (UCMD) at the severe end.

This problem is solved by the use of a compound of formula (I)

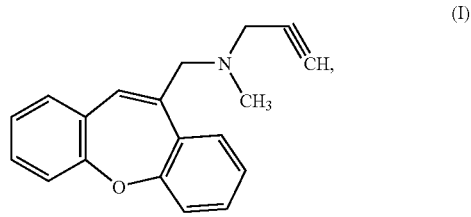

or a pharmaceutically acceptable addition salt thereof for the preparation of a medicament for the prophylaxis and/or treatment of muscular dystrophy.

The compound of formula (I) or an addition salt thereof is preferably used for the prophylaxis and/or treatment of congenital muscular dystrophies, in particular Bethlem myopathy (BM) or Ullrich congenital muscular dystrophy (UCMD) resulting from mutations in the genes encoding for collagen VI-A1 (Col6A1), collagen VI-A2 (Col6A2) or collagen VI-A3 (Col6A3), respectively.

The compound of formula (I) is N-(dibenz(b,f)oxepin-10-ylmethyl)-N-methyl-N-prop-2-ynylamine, also known as omigapil. The compound of formula (I) or salts thereof has been proposed and investigated as potential treatment option for various neurodegenerative diseases in which apoptotic cytolysis plays a role. Such neurodegenerative diseases include cerebral ischemia, Alzheimer's disease, Huntington's disease and Parkinson's disease, amyotrophic lateral sclerosis, multiple sclerosis, types of glaucoma, retina degeneration, as well as general or diabetic peripheral neuropathy. The use of the compound of formula (I) or salts thereof for the treatment of these diseases as well as processes for the preparation of omigapil are disclosed in WO 97/45422, EP-A-0726265, WO 2004/066993 and WO 2005/044255. It has furthermore been reported that the compound of formula (I) binds to glyceraldehyde-3-phosphate dehydrogenase (GAPDH) and exerts antiapoptotic effects (Kragten E et al. (1998)—Glyceraldehyde-3-phosphate dehydrogenase, the putative target of the antiapoptotic compounds CGP 3466 and R(−)deprenyl. *J. Biol. Chem.* 273:5821-5828).

The pharmaceutically acceptable addition salt of the compound of formula (I) is preferably a salt of a mineral acid or an organic carboxylic acid. In a more preferred embodiment the organic carboxylic acid is an optionally hydroxylated ($C_{1-7}$) alkanoic acid, an optionally hydroxylated, aminated and/or oxo-substituted ($C_{2-7}$)alkane-dicarboxylic acid, an optionally hydroxylated and/or oxo-substituted ($C_{3-7}$)alkane-tricarboxylic acid, an optionally hydroxylated and/or oxo-substituted ($C_{4-7}$)alkene-dicarboxylic acid, optionally hydroxylated and/or oxo-substituted ($C_{4-7}$)alkine-dicarboxylic acid, an aliphatic or aromatic sulfonic acid, or an aliphatic or aromatic N-substituted sulfamic acid.

In a further preferred embodiment the addition salt of the compound of formula (I) contains an anion selected from the group consisting of chloride, perchlorate, bromide, iodide, nitrate, phosphate, acid phosphate, sulfate, methanesulfonate, ethanesulfonate, benzenesulfonate, p-toluenesulfonate, naphthalene-2-sulfonate, bisulfate, N-cyclohexylsulfamate, carbonate, formate, acetate, propionate, pivalate, glycolate, lactate, gluconate, glucuronate, ascorbate, pantothenate, oxalate, malonate, succinate, glutamate, aspartate, tartrate, bitartrate, malate, citrate, aconate, fumarate, maleate, itaconate, acetylene dicarboxylate, benzoate, salicylate, phthalate, phenylacetate, mandelate, cinnamate, p-hydroxybenzoate, 2,5-dihydroxy-benzoate, p-methoxybenzoate, hydroxy naphthoate, nicotinate, isonicotinate and saccharate.

In another preferred embodiment the addition salt of the compound of formula (I) contains a cation selected from the group consisting of $H^+$, $Na^+$ and $K^+$.

The maleate of the compound of formula (I), i.e. N-(dibenz(b,f)oxepin-10-ylmethyl)-N-methyl-N-prop-2-ynylammonium maleate, is particularly preferred. This compound is also known as omigapil, CGP 3466 or TCH346.

The present invention is also directed to a method for therapeutic and/or prophylactic treatment of a mammal requiring treatment, by administration of an effective amount of a compound of formula (I) or a pharmaceutically acceptable addition salt thereof for the prophylaxis and/or treatment of muscular dystrophy, preferably muscular dystrophies or myopathies resulting from mutations in the genes encoding for collagen VI (Col6A1-3) clinically described as forms of Ullrich congenital muscular dystrophy or Bethlem myopathy.

It is preferred that the compound of formula (I) or a pharmaceutically acceptable addition salt thereof is used together with a second therapeutic agent. More preferably the second therapeutic agent is any medicament used in UCMD or BM patients to treat pathological manifestations of muscle weakness resulting from collagen VI deficiency. Even more preferably, the second therapeutic agent is selected from the group consisting of idebenone (2,3-dimethoxy-5-methyl-6-(10-hydroxydecyl)-1,4-benzoquinone), gluco-corticosteroids, and anti-infectives. The glucocorticosteroid is for example 6α-methylprednisolone-21 sodium succinate (Solumedrol®) or deflazacort (Calcort®). The anti-infectives are suitably selected from anti-infectives which are routinely used for the treatment of respiratory infections in BM or UCMD patients.

The compound of formula (I) or a pharmaceutically acceptable addition salt thereof and the second therapeutic agent can be used simultaneously, separately or sequentially in order to prevent or treat the disease symptoms. The two therapeutic agents may be provided in a single dosage form or a separate formulation, each formulation containing at least one of the two therapeutic agents.

The compound of formula (I) or a pharmaceutically acceptable addition salt thereof is preferably used for treating or preventing weakness and loss of skeletal muscle tissue associated with congenital muscular dystrophy or myopathy resulting from collagen VI deficiency, in particular UCMD or BM. Specifically, the invention relates to the use of a compound of formula (I) or a pharmaceutically acceptable addition salt thereof for treating UCMD or BM and clinically intermediate forms of muscular dystrophies or myopathies resulting from mutations in the Col6A1-3 genes by administering an effective amount of the compound of formula (I) or a pharmaceutically acceptable addition salt thereof, preferably N-(dibenzo[b,f]oxepin-10-ylmethyl)-N-methyl-N-prop-2-inyl-ammonium salts and in particular N-(dibenzo[b,f]oxepin-10-ylmethyl)-N-methyl-N-prop-2-inyl-ammonium maleate.

The effective dosage of the active ingredient employed may vary depending on the particular compounds employed, the mode of administration, the condition being treated and the severity of the condition being treated. Such dosage may be ascertained readily by a person skilled in the art. In humans the compound of formula (I) or a pharmaceutically acceptable addition salt thereof is preferably administered in a dosage range of 0.01 mg/day to 80 mg/day, more preferably in a dosage range of 0.05 mg/day to 40 mg/day and most preferred in a dosage range of 0.1 mg/day to 20 mg/day.

Further, the compound of formula (I) or a pharmaceutically acceptable addition salt thereof is preferably administered at least once a day, preferably for at least 3 months, more preferably for at least 6 months, most preferably for 6 months to 12 months to observe the initial amelioration of the disease symptoms (as for example but not exclusively amelioration of muscle weakness, respiratory problems) associated with UCMD and BM resulting from collagen VI deficiency. For maintenance of the therapeutic effect prolonged treatment is recommended; the preferred treatment is lifelong.

Any suitable route of administration may be employed for providing a mammal, especially a human, with an effective dosage of the compound of formula (I) or a pharmaceutically acceptable addition salt thereof. The modes of administration include rectal, topical, ocular, pulmonary, oral, intraperitoneal (i.p.), intravenous (i.v.), intramuscular (i.m.), intracavernous (i.c.), parenteral, intranasal and transdermal. Preferred modes of administration are oral, intraperitoneal, intravenous, intramuscular, intracavernous, parenteral, intranasal and transdermal, whereas the oral administration is the most preferred mode of administration.

The compound of formula (I) or a pharmaceutically acceptable addition salt thereof is preferably formulated into a dosage form prior to administration. The dosage forms include, e.g., tablets, pills, granules, powders, lozenges, sachets, cachets, elixirs, aqueous and oil-based suspensions, emulsions, dispersions, solutions such as sterile injectable solutions, syrups, aerosols (as a solid or in a liquid medium), capsules such as soft and hard gelatin capsules, suppositories, sterile packaged powders, troches, creams, ointments and aerosols. Tablets are most preferred.

For oral application suitable preparations are in the form of tablets, sugar-coated pills, capsules, granular powders, drops, juices and syrups, while for parenteral, topical and inhalative application suitable forms are solutions, suspensions, easily reconstitutable dry preparations as well as sprays.

Accordingly, the compound of formula (I) or a pharmaceutically acceptable addition salt thereof may be combined with any suitable pharmaceutical carrier. The pharmaceutical preparations for use in accordance with the present invention may be prepared by normal procedures using well-known and readily available ingredients. Such ingredients can be excipients, fillers, solvents, diluents, dyes and/or binders.

In making the formulations, the compound of formula (I) or a pharmaceutically acceptable addition salt thereof is usually mixed with a carrier, or diluted by a carrier, or enclosed with a carrier, which may be in the form of a capsule, cachet, paper or other container.

When the carrier serves as a diluent, it may be a solid, semi-solid, or liquid material, which acts as a vehicle, excipient or medium for the active ingredient.

Some examples of suitable carriers, excipients and diluents include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water syrup, methyl cellulose, methyl and propylhydroxybenzoates, talc, magnesium stearate and mineral oil.

The formulations can additionally include lubricating agents, wetting agents, emulsifying and suspending agents, preserving agents, sweetening agents and/or flavoring agents.

The choice of auxiliary substances as well as the amounts thereof to be used depends on whether the medicinal drug is to be administered orally, intravenously, intraperitoneally, intradermally, intramuscularly, intranasally, buccally or topically.

The compound of formula (I) or a pharmaceutically acceptable addition salt thereof may be formulated so as to provide quick, sustained or delayed release of the active ingredient after administration to the patient. To this end, the compound of formula (I) or a pharmaceutically acceptable addition salt thereof can for example be administered in a sustained-release substance, in dissolved form or in a plaster, optionally with the addition of agents promoting penetration of the skin, and are suitable as percutaneous application preparations. Forms of preparations that can be used orally or percutaneously may produce a delayed release of the compounds.

The compound of formula (I) or a pharmaceutically acceptable addition salt thereof is toxically safe which means that it can be used as a pharmaceutical active agent in a medicament.

The following examples further illustrate the invention.

Animal Model of Myopathy Resulting from Collagen VI Deficiency

Inactivation of the collagen VI-A1 (Col6a1) gene by targeted gene disruption resulted in a mouse model for BM and UCMD (Bonaldo P. et al. (1998) Collagen VI deficiency induces early onset myopathy in the mouse: an animal model for Bethlem myopathy. Hum Mol Genet. 7: 2135-2140). Homozyguous col6a1−/− mutants lack triple-helical collagen VI resulting in a phenotype that resembles BM/UCMD in human patients with collagen VI deficiency. Specifically, col6a1−/− mice show histological features of myopathy such as fiber necrosis and phagocytosis and a pronounced variation in fiber diameter. Muscles also show signs of stimulated regeneration of fibers and necrotic fibers are particularly frequent in the diaphragm thereby resembling more the clinical picture of UCMD than BM (Bertini E., Pepe G. (2002) Collagen type VI and related disorders: Bethlem myopathy and Ullrich scleroatonic muscular dystrophy Europ. J. Paediatric Neurology 6:193-198). Further investigation of col6a1−/− mice demonstrated that muscles have a loss of contractile strength associated with ultrastructural alterations of the sarcoplasmic reticulum and mitochondria (Irwin W A et al. (2003) Mitochondrial dysfunction and apoptosis in myopathic mice with collagen VI deficiency. Nature Genetics 35:367-371). This mitochondrial dysfunction might be caused by slight increase in of sarcolemmal calcium influx followed by calcium overload eventually causing opening of the mitochondrial permeability transition pore (MPTP) and finally apoptosis.

EXAMPLE 1

The effect of N-(dibenz(b,f)oxepin-10-ylmethyl)-N-methyl-N-prop-2-ynylammonium maleate (omigapil) was tested on the number of apoptotic nuclei in muscle of a Col6a1-deficient mouse model. Starting at 16±4 weeks of age, homozygous col6a1−/− mice were treated with omigapil. For this, omigapil was dissolved in 1% w/v ethanol to a final concentration of 20 μg/ml. Mutant mice received a final dose of 1 mg/kg or 10 mg/kg omigapil given twice daily by gavage following the guidance as described elsewhere (Sagot Y. et al. (2000) An orally active anti-apoptotic molecule (CGP 3466B) preserves mitochondria and enhances survival in an animal model of motoneuron disease. *Br. J. Pharmacol.* 131: 721-728). For comparison col6a1−/− mice received the equivalent amount of vehicle only. After five days of application mice were sacrificed, the diaphragm removed, sectioned and stained for apoptotic nuclei using TUNEL staining. The number of apoptotic nuclei per mm2 area in the diaphragm muscle was determined as described (Irwin W A et al. (2003) Mitochondrial dysfunction and apoptosis in myopathic mice with collagen VI deficiency. Nature Genetics 35:367-371).

Figure 1:
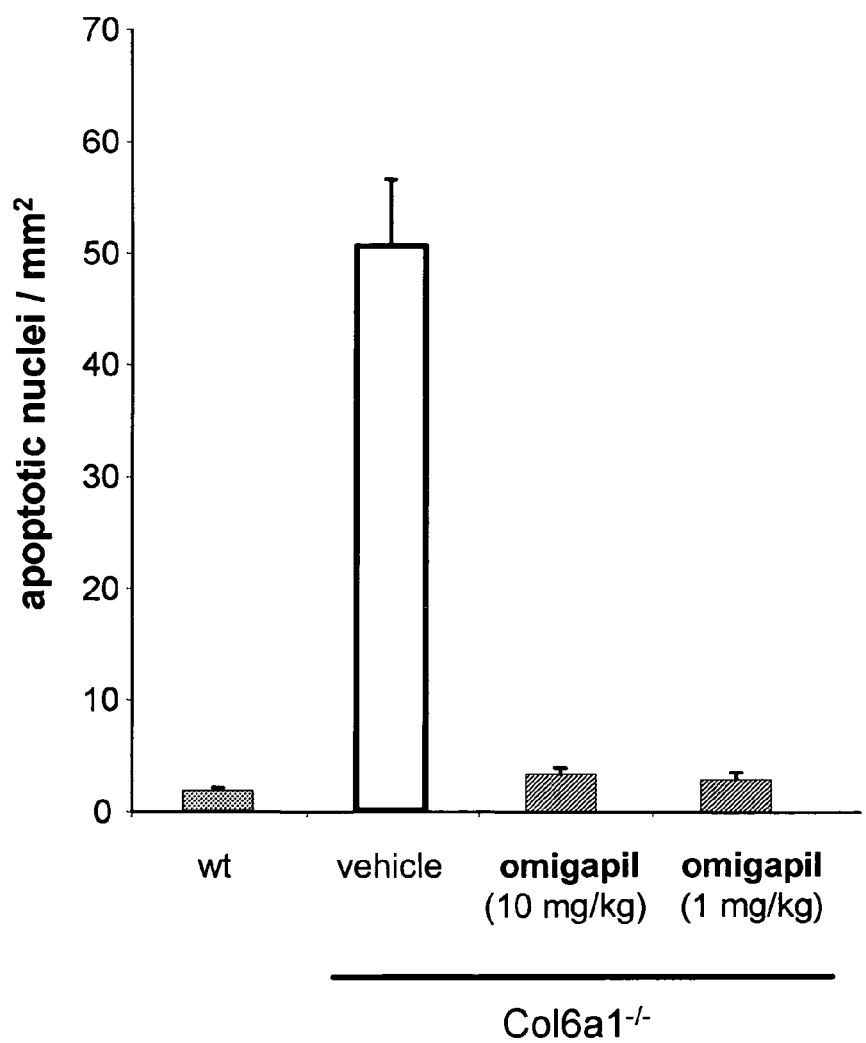
FIG. 1 is a graph which shows the number of apoptotic nuclei in diaphragm muscles of col6a1−/− mice treated for 5 days with omigapil at a dose of 1 mg/kg or 10 mg/kg as compared to vehicle-treated col6a1−/− mice.

Surprisingly it was found that omigapil significantly reduced the number of apoptotic (i.e. TUNEL assay positive) nuclei in diaphragm muscle. As demonstrated in FIG. 1, omigapil significantly reduced the number of apoptotic nuclei in diaphragm muscle of col6a1−/− mice treated for 5 days with omigapil at a dose of 1 mg/kg (N=3) or 10 mg/kg (N=4) as compared to vehicle treated col6a1−/− mice (N=6). It is surprising that the number of apoptotic nuclei in omigapil-treated animals was comparable to the number seen in diaphragm muscle of a wild-type animal (i.e. mice not carrying the mutation in the collagen VI-A1 gene).

It is particularly surprising that omigapil reduces the number of apoptotic nuclei in muscle of Col6A1-deficient mice since it is not obvious to the skilled artist that inhibition of GAPDH may hold the potential to prevent apoptosis in an animal model for BM and UCMD. The involvement of GAPDH mediated cell signaling processes (Hara M R et al. (2005); S-nitrosylated GAPDH initiates apoptotic cell death by nuclear translocation following Siah1 binding, Nature Cell Biol 7:665-674) have not been implicated in muscular dystrophies associated with collagen VI-deficiency and there is currently no evidence that GAPDH is involved in the pathology caused by gene mutations in either the collagen VI-A1, collagen VI-A2 or collagen VI-A3 genes resulting in Bethlem myopathy or Ullrich CMD. The surprising finding that omigapil can protect from apoptosis of muscle cells in collagen VI-deficient tissue holds the potential for a omigapil-based therapeutic intervention in BM and UCMD patients where apoptosis has also been reported (Hayashi Y K., et al. (2001) Massive muscle cell degeneration in the early stage of merosin-deficient congenital muscular dystrophy. Neuromuscul. Disord. 11: 350-359).

EXAMPLE 2

The effect of N-(dibenz(b,f)oxepin-10-ylmethyl)-N-methyl-N-prop-2-ynylammonium maleate (omigapil) was tested on the effect to normalize ultrastructural defects in mitochondria of a Col6a1-deficient mouse model. For this, Col6a1-deficient mice were treated with omigapil as described in Example 1.

The ultrastructural appearance of mitochondria in muscle fibers of the diaphragm muscle was determined and quantified as described (Irwin W A et al. (2003) Mitochondrial dysfunction and apoptosis in myopathic mice with collagen VI deficiency. Nature Genetics 35:367-371).

Figure 2:
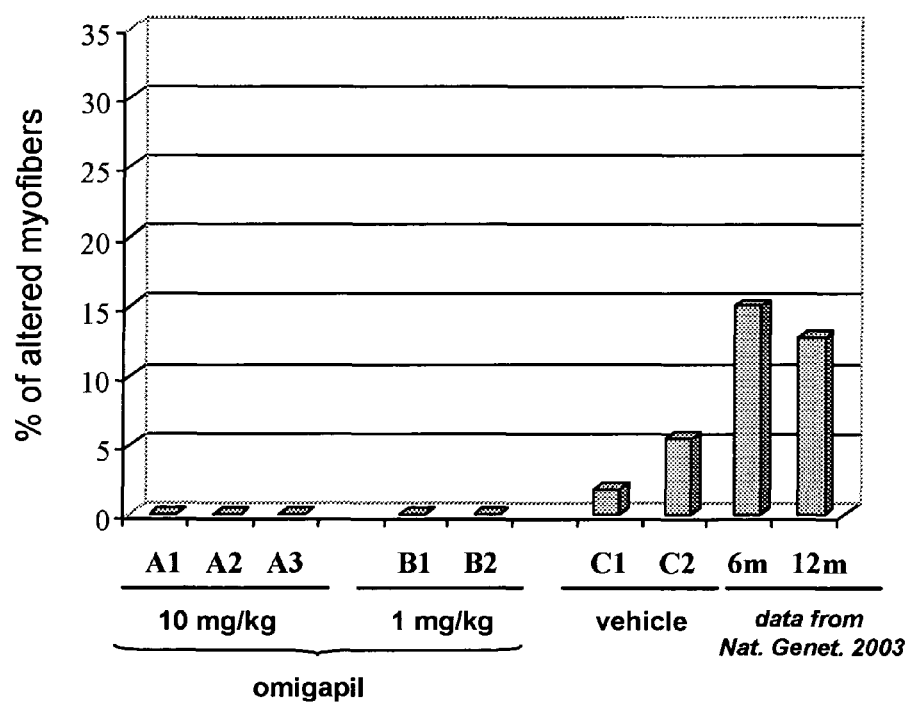
FIG. 2 is a graph which shows the percentage of myofibers with pathologically altered mitochondria treated with omigapil at doses of 10 mg/kg or 1 mg/kg compared to vehicle-treated animals.

Surprisingly it was found that omigapil normalized the ultrastructural appearance of mitochondria in muscle fibers of the diaphragm muscle. Specifically, the percentage of myofibers with pathologically altered mitochondria was clearly reduced with omigapil at doses of 10 mg/kg (animals A1-A3, FIG. 2) or 1 mg/kg (animals B1-B2, FIG. 2) compared to vehicle-treated animals (animals $C_1$-$C_2$, FIG. 2).

It is surprising that omigapil can normalize the pathological changes at the ultrastructural level in mitochondria of muscle tissue in col6a1-/- mice.

This normalization of mitochondrial abnormalities clearly is of therapeutic relevance and opens an omigapil-based therapeutic intervention for BM and UCMD.

The invention claimed is:

1. A method of treating muscular dystrophy in a mammal, which method comprises administering to a mammal a compound of formula (I)

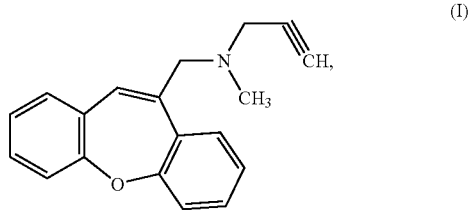

(I)

or a pharmaceutically acceptable addition salt thereof, whereupon muscular dystrophy is treated in the mammal.

2. The method of claim 1, wherein the muscular dystrophy is a congenital muscular dystrophy or myopathy resulting from mutations in any of the collagen VI genes selected from the group consisting of Col6A1, Col6A2, and Col6A3.

3. The method of claim 2, wherein the muscular dystrophy is Ullrich congenital muscular dystrophy, Bethlem myopathy, or intermediate clinical manifestations thereof.

4. The method of claim 1, wherein the salt of the compound of formula (I) is a salt of a mineral acid or an organic carboxylic acid.

5. The method of claim 4, wherein the organic carboxylic acid is an optionally hydroxylated ($C_{1-7}$)alkanoic acid, an optionally hydroxylated, aminated and/or oxo-substituted ($C_{2-7}$)alkane-dicarboxylic acid, an optionally hydroxylated and/or oxo-substituted ($C_{3-7}$)alkane-tricarboxylic acid, an optionally hydroxylated and/or oxo-substituted ($C_{4-7}$)alkene-dicarboxylic acid, optionally hydroxylated and/or oxo-substituted ($C_{4-7}$)alkine-dicarboxylic acid, an aliphatic or aromatic sulfonic acid, or an aliphatic or aromatic N-substituted sulfamic acid.

6. The method of claim 1, wherein the salt of the compound of formula (I) contains an anion selected from the group consisting of chloride, perchlorate, bromide, iodide, nitrate, phosphate, acid phosphate, sulfate, methanesulfonate, ethanesulfonate, benzenesulfonate, p-toluenesulfonate, naphthalene-2-sulfonate, bisulfate, N-cyclohexyl-sulfamate, carbonate, formate, acetate, propionate, pivalate, glycolate, lactate, gluconate, glucuronate, ascorbate, pantothenate, oxalate, malonate, succinate, glutamate, aspartate, tartrate, bitartrate, malate, citrate, aconate, fumarate, maleate, itaconate, acetylene dicarboxylate, benzoate, salicylate, phthalate, phenylacetate, mandelate, cinnamate, p-hydroxybenzoate, 2,5-dihydroxy-benzoate, p-methoxybenzoate, hydroxy naphthoate, nicotinate, isonicotinate and saccharate.

7. The method of claim 1, wherein the salt of the compound of formula (I) contains a cation selected from the group consisting of $H^+$, $Na^+$ and $K^+$.

8. The method of claim 1, wherein the compound is the maleate salt of the compound of formula (I).

9. The method of claim 1, wherein the compound of formula (I) or a pharmaceutically acceptable addition salt thereof is administered orally in form of a tablet.

10. The method of claim 1, wherein the compound of formula (I) or a pharmaceutically acceptable addition salt thereof is administered to the mammal in combination with a second therapeutic agent.

11. The method of claim 10, wherein the second therapeutic agent is selected from the group consisting of idebenone (2,3-dimethoxy-5-methyl-6-(10-hydroxydecyl)-1,4-benzoquinone), glucocorticosteroids, and antiinfectives.

* * * * *